(12) United States Patent
Jung et al.

(10) Patent No.: US 7,182,788 B2
(45) Date of Patent: Feb. 27, 2007

(54) STENT AND METHOD FOR MANUFACTURING THE SAME

(75) Inventors: In-Kwon Jung, Pyongtaek (KR); Sung-Soon An, Seoul (KR); Hun-Kuk Park, Pyongtaek (KR)

(73) Assignee: M. I. Tech Co., Ltd., Pyongtack (KR)

( * ) Notice: Subject to any disclaimer, the term of this patent is extended or adjusted under 35 U.S.C. 154(b) by 177 days.

(21) Appl. No.: 10/461,902

(22) Filed: Jun. 13, 2003

(65) Prior Publication Data

US 2004/0044402 A1 Mar. 4, 2004

(30) Foreign Application Priority Data

Sep. 3, 2002 (KR) ...................... 10-2002-0052868

(51) Int. Cl.
*A61F 2/04* (2006.01)
(52) U.S. Cl. .................................................. 623/23.68
(58) Field of Classification Search ............... 623/1.24, 623/1.25, 1.26, 2.12, 2.13, 2.14, 2.15, 2.16, 623/2.17, 2.18, 2.19, 23.68
See application file for complete search history.

(56) References Cited

U.S. PATENT DOCUMENTS

| | | | |
|---|---|---|---|
| 3,755,823 A | 9/1973 | Hancock | |
| 4,580,568 A | 4/1986 | Gianturco | |
| 5,840,081 A | 11/1998 | Andersen et al. | |
| 6,168,614 B1 | 1/2001 | Andersen et al. | |
| 6,264,700 B1 * | 7/2001 | Kilcoyne et al. | 623/23.68 |
| 2001/0020189 A1 | 9/2001 | Taylor | |

FOREIGN PATENT DOCUMENTS

| | | |
|---|---|---|
| EP | 0 808 614 | 11/1997 |
| JP | 10-043315 | 2/1998 |
| JP | 11-299795 | 11/1999 |
| JP | 2001-327609 | 11/2001 |
| WO | WO 01/19285 | 3/2001 |
| WO | WO 01/54625 A1 | 8/2001 |
| WO | WO 01/66043 | 9/2001 |
| WO | WO 02/45933 A2 | 6/2002 |
| WO | WO 02/45933 A3 | 6/2002 |

OTHER PUBLICATIONS

Search Report for corresponding European Application No. 03013328.4 dated Apr. 21, 2005.

* cited by examiner

*Primary Examiner*—Corrine McDermott
*Assistant Examiner*—Thomas J Sweet
(74) *Attorney, Agent, or Firm*—Alston & Bird LLP

(57) ABSTRACT

A stent includes a cylindrical main body contractible and expandable in a circumferential direction, a cover member coated on inner and/or outer circumference of the main body, and an inverse current preventing member for preventing food or fluid from reversely flowing. The inverse current preventing member is disposed in the main body and includes a fixing layer defining a passage having a diameter capable of allowing food and fluid to pass, the fixing layer being fixed in the main body and a valve layer extending from the fixing layer to a distal end of the main body.

8 Claims, 13 Drawing Sheets

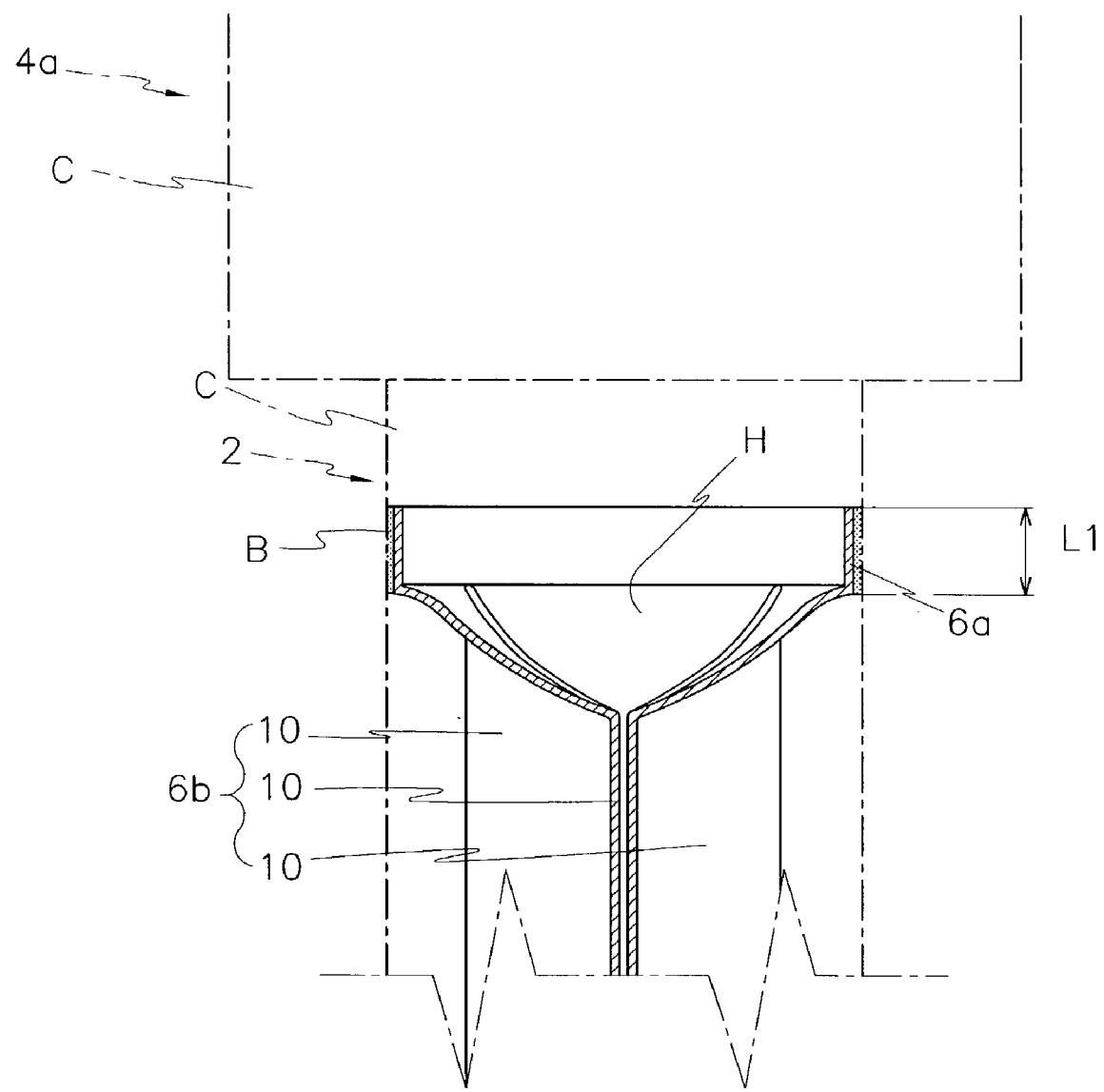

STENT AND METHOD FOR MANUFACTURING THE SAME

CROSS-REFERENCE TO RELATED APPLICATIONS

The present application claims priority from Korean Patent Application No. 10-2002-0052868, filed on Sep. 3, 2002.

BACKGROUND OF THE INVENTION

1 Field of the Invention

The present invention relates to a stent for implantation in a body lumen and, more particularly, to a stent that is designed to, when it is implanted in the body lumen, enhance its reliability and minimize the medical side effect by assisting the function of the body lumen and preventing the inverse current of food or fluid input in the body. The present invention further relates to a method for manufacturing such a stent.

2 Description of Prior Art

Stents are generally tubular-shaped devices which function to hold open a segment of a blood vessel or other anatomical lumen. They are particularly suitable for use to support and hold back a dissected arterial lining which can occlude the fluid passageway therethrough.

A variety of stents are well known in the art. The stents are classified in an elastic stent and a plastic stent. The former is designed to be contracted by outer force and to be self-expanded when the outer force is released. The latter is designed to keep its deformed state unless outer force is applied thereto.

The stent is required to perform various functions according to a location of the body lumen it is to be implanted. For example, there is a sphincteral muscle for the esophageal orifice on a connecting portion of the stomach and the esophagus. The sphincteral muscle prevents the food and fluid from reversely flowing. Therefore, when the stent is implanted on the sphincteral muscle, the sphincteral muscle loses its inverse current preventing function. Therefore, the stent to be implanted on the sphincteral muscle for the esophageal orifice should be provided with means for preventing the inverse current, thereby preventing the medical side effect caused by the inverse current of the food and fluid.

A variety of prior art stents having the inverse preventing means can be found in U.S. Pat. Nos. 3,755,823, 4,580,568, 5,840,081 and 6,168,614.

However, since the prior art stents having the inverse preventing means have short valve plates integrally coupled on an inner circumference of the stent, the valve plates may be deformed or warped by outer force when the stent is implanted in the body lumen, making the valve plates opened regardless of the supply of the food and fluid input.

Furthermore, the inverse current preventing means disclosed in the prior art stents has valve plates that should be bonded on the inner circumference of the stent by adhesive, requiring a bonding space for the bonding process to make it difficult to manufacture the same.

In addition, a prior art stent having the inverse current preventing means that is formed on an outer circumference of the stent is also proposed. However, since the inverse current preventing means stimulates the inner wall of the stomach, a medical problem may occur.

SUMMARY OF THE INVENTION

Therefore, the present invention has been made in an effort to solve the above described problems of the prior art.

It is a first objective of the present invention to provide a stent that can, when it is implanted in the body lumen, assist the function of the body lumen to reliably prevent the food and fluid from reversely flowing.

It is a second objective of the present invention to provide a method for more effectively manufacturing such a stent.

To achieve the first objective, the present invention provides a stent comprising a cylindrical main body contractible and expandable in a circumferential direction; a cover member coated on inner and/or outer circumference of the main body; and inverse current preventing means for preventing food or fluid from reversely flowing, the inverse current preventing means being disposed in the main body, wherein the inverse current preventing means comprises: a fixing layer defining a passage having a diameter capable of allowing food and fluid to pass, the fixing layer being fixed in the main body; and a valve layer extending from the fixing layer to a distal end of the main body.

Preferably, the valve layer is comprised of at least one extended wing defined by folding the valve layer.

The extended wing is extending radially from a central axis of the main body, the extended wing being formed in one of an inline shape, a wave shape, and a sawtooth shape.

Preferably, a length of the valve layer is about 150% of a diameter of the main body or above 20% of a whole length of the stent.

The inverse current preventing means is formed of material selected from the group consisting of medical Polyurethane, Silicone-Urethane copolymer, Silicone, Polyamide, Polyester, fluoric resin.

The cover member is formed of material selected from the group consisting of medical Polyurethane, Silicone-Urethane copolymer, Silicone, Polyamide, Polyester, fluoric resin.

The stent may further comprise sub-bodies for preventing the main body from displacing from an implanted position of a body lumen, the sub-bodies being formed on opposite ends of the main body.

The valve layer of the inverse current preventing means is fixed on at least one point of the cover member.

To achieve the second objective, the present invention provides a method for manufacturing a stent, comprising the steps of preparing a cylindrical main body contractible and expandable in a circumferential direction; forming a cover member on an inner and/or outer circumference of the main body; locating inverse current preventing means formed by a casting process in the main body; and bonding the located inverse current preventing means on the inner circumference of the main body.

Preferably, the step of bonding is realized by an adhesive solution or by a thermal bonding process.

The adhesive solution contains solvent selected from the group consisting of DMAC (N, N-DIMETHYLACETAMIDE), DMF (N,N-DIMETHYLFORMAMIDE), DMSO (DIMETHYLSULFOXIDE), THF (TETRAHYDROFURAN), XYLENE, TOLUENE, and CHLOROFORM. An amount of the solvent contained in the solution is 3–70 w %.

Preferably, the thermal bonding process is selected when the cover member and the inverse current preventing means are formed of fluoric resin.

The inverse current preventing means is further fixed at a sub-bonding point formed on the inner circumference of the main body in the longitudinal direction.

BRIEF DESCRIPTION OF THE DRAWINGS

FIG. 1b is a block diagram illustrating a bonding process of FIG. 1a;

FIG. 4a is a side view of FIG. 3a;

FIG. 4b is an enlarged view illustrating a major part of FIG. 4a;

DETAILED DESCRIPTION OF THE PREFERRED EMBODIMENTS

Preferred embodiments of the present invention will be described more in detail hereafter in conjunction with the accompanying drawings.

Figure 1A:
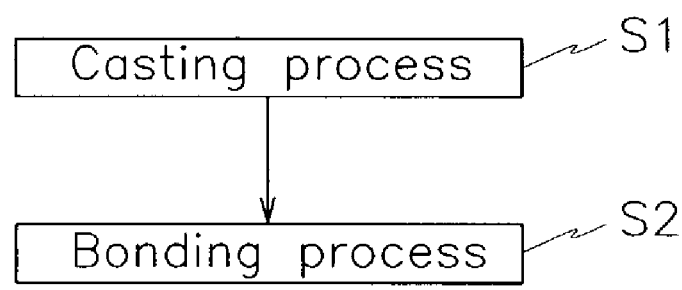
FIG. 1a is a block diagram illustrating a method for manufacturing a stent according to a preferred embodiment of the present invention.
Figure 1B:
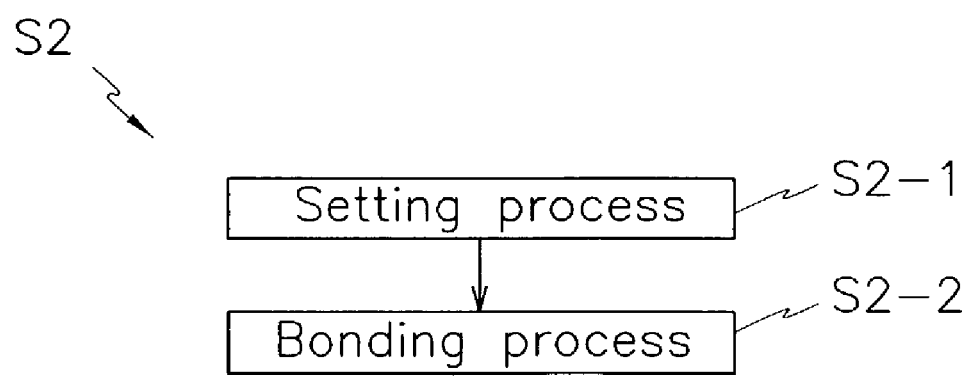
Figure 2:
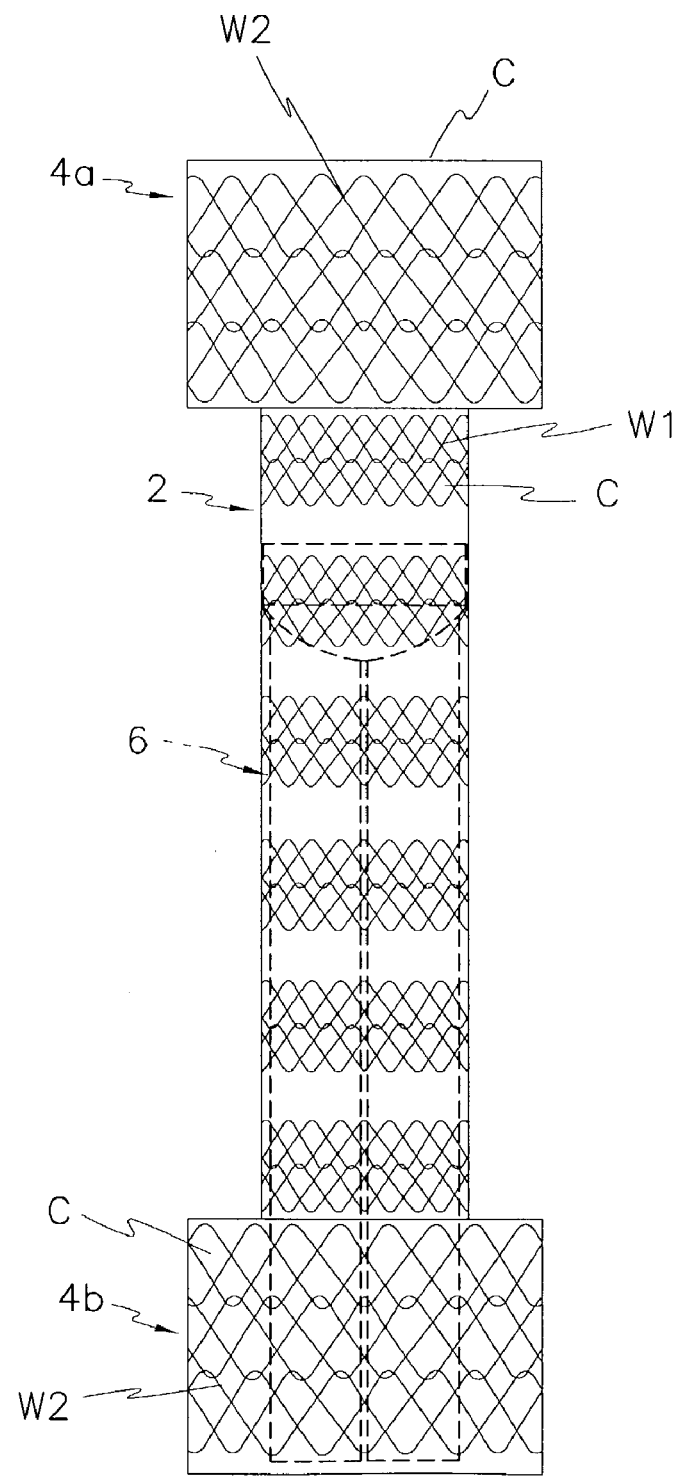
FIG. 2 is a front view of a stent manufactured under the process depicted in FIGS. 1a and 1b.
Figure 3A:
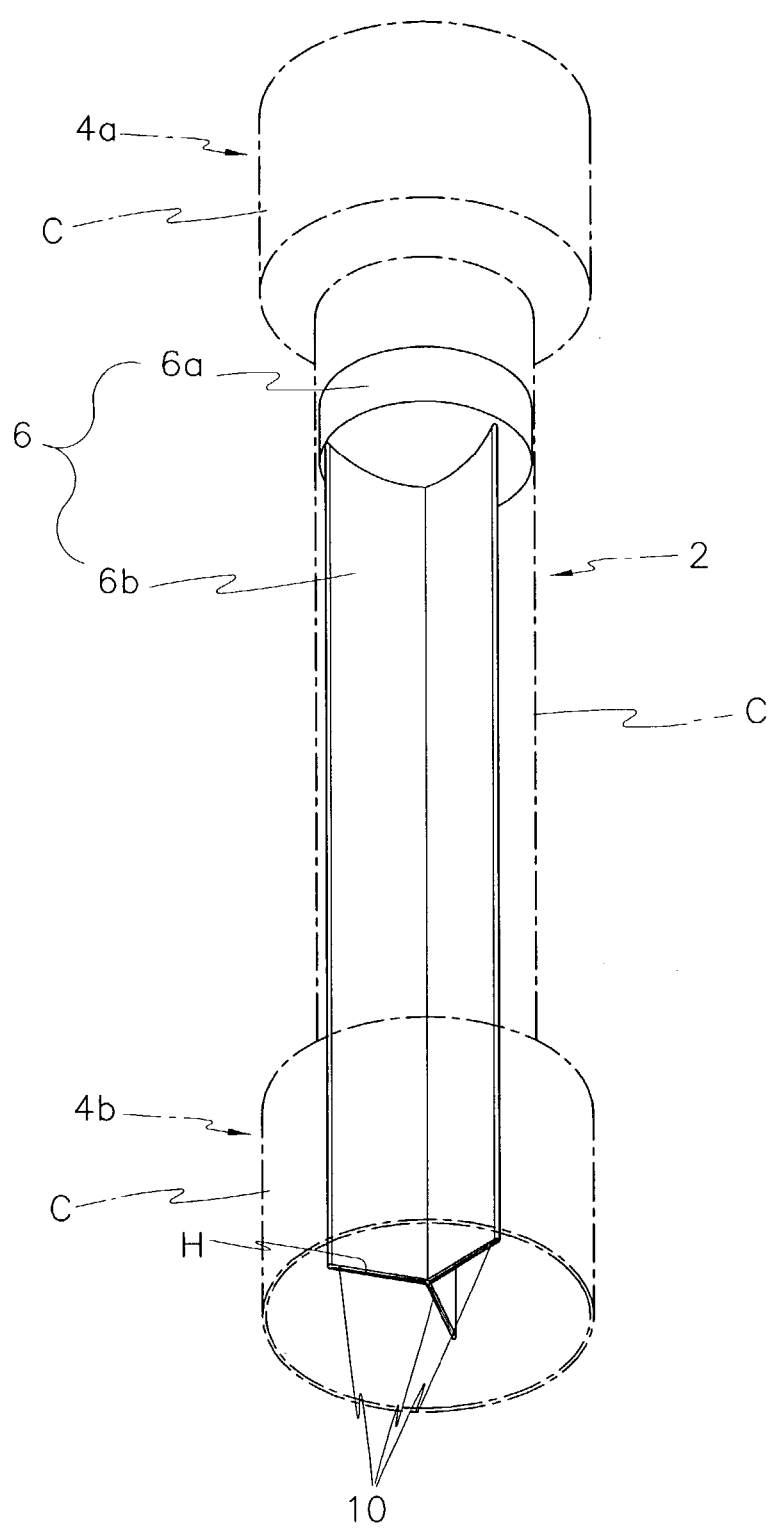
FIG. 3a is a perspective view illustrating an inner structure of a stent depicted in FIG. 2.
Figure 3B:
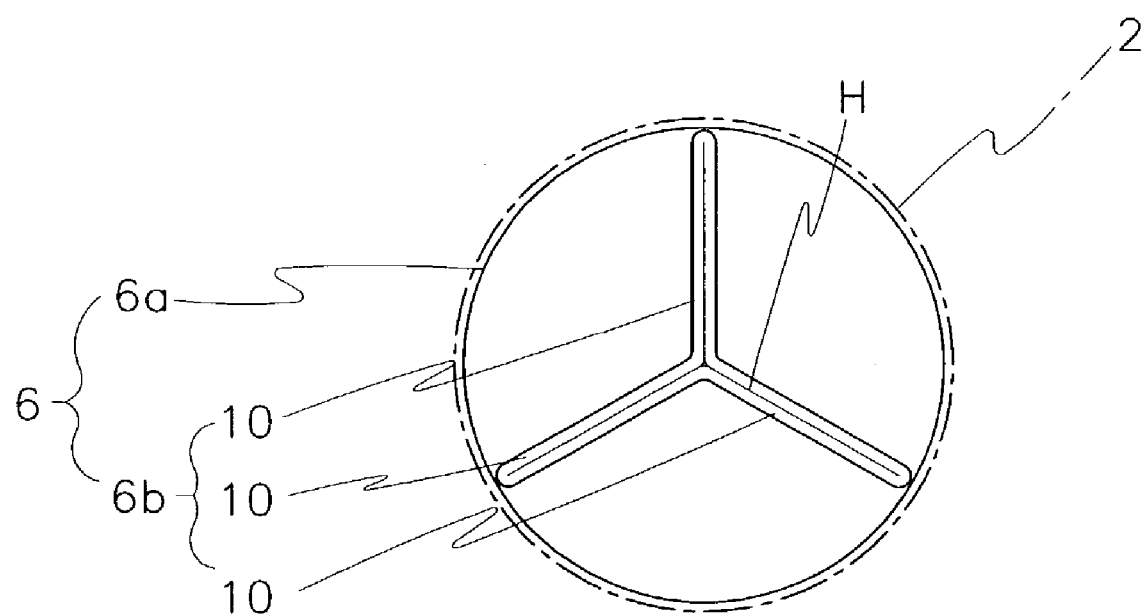
FIG. 3b is a bottom view of FIG. 2.
Figure 4A:
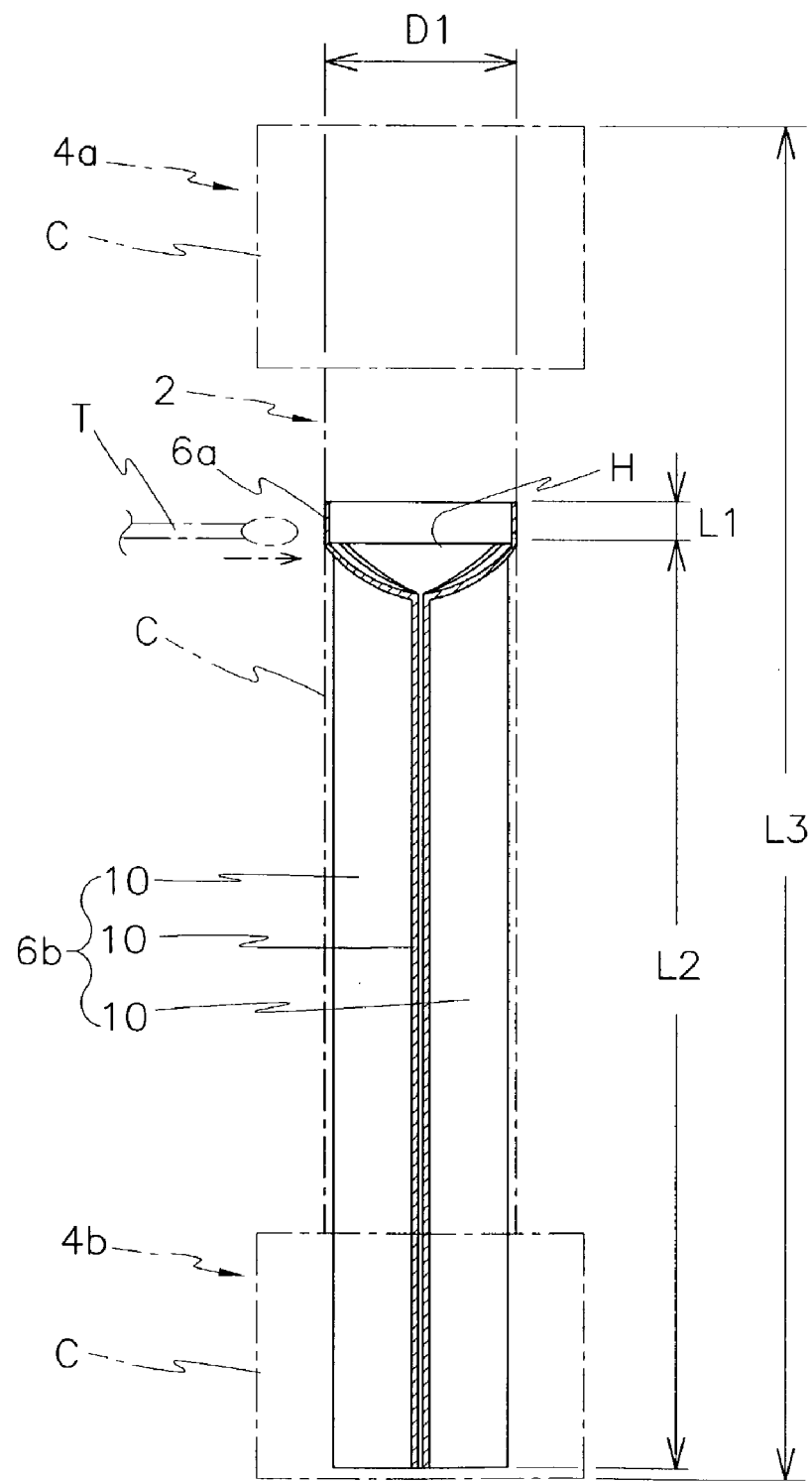

FIGS. 1a and 1b show a method for manufacturing a stent according to a preferred embodiment of the present invention and FIGS. 2, 3a and 3b show a stent manufactured by the method depicted in FIGS. 1a and 1b.

As shown in the drawings, a stent of the present invention comprises a cylindrical main body 2 having a diameter insertable into a body lumen, a cover member C enclosing inner and outer circumferences of the main body 2, and inverse current preventing means disposed inside the main body 2 for preventing the food and fluid from reversely flowing.

The cylindrical main body 2 is implanted in a body lumen (i.e., a connecting portion of the stomach and the esophagus) to obtain a passage of the body lumen that is stenosed by disease. The size (the diameter and length) of the main body 2 is determined depending on the stenosed location and state of the body lumen.

The main body 2 is formed of a wire member W1 that is bent in a zigzag and endlessly connected to define a cylindrical shape. The main body 2 is a well known structure, which is designed such that when outer force is applied to the main body 2, it is elastically deformed, and when the outer force is released, it is returned to its initial shape by self-elastic force.

However, the main body 2 is not limited to the above-described structure. Any types of well known structure can be employed as the main body 2. Since the structure of the main body is already used for a variety of medical stents, the detailed description thereof will be omitted herein.

Figure 7A:
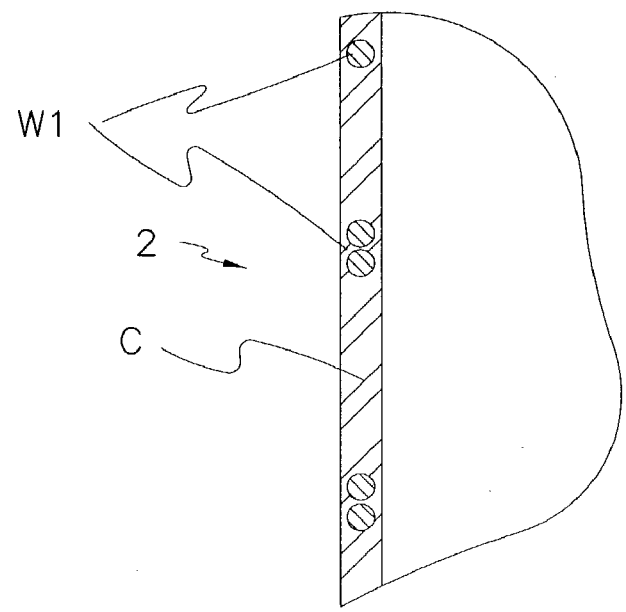
FIG. 7a is an enlarged sectional view of a main body of a stent depicted in FIG. 1.

As shown in FIGS. 2, 3a and 7a, the main body 2 formed by the wire member W1 is covered with the cover member C. The cover member C prevents the wire member W1 from directly contacting the body lumen and also prevents abnormal tissue such as the cancer from penetrating into and blocking the passage of the stent.

The coating of the cover member C on around the wire member W1 can be realized by a solvent-casting (casting process S1). The solvent-casting is a forming method of a thin film layer. That is, the cover member C is formed by depositing solution containing a solvent such as DMAC(N, N-Dimethyformamide), DMSO(Dimethylsulfoxide), THF (Tetrahydrofuran), Sylene, Toluene, and Chloroform on a surface of a mold formed in a predetermined shape.

The cover member C is generally formed of medical polyurethane, silicone-urethane copolymer, silicon, polyamide, polyester or fluoric resin. However, other materials that can be easily deformed by outer force and particularly has biocompatibility to minimize the side effect can also be used.

Referring to accompanying drawings, sub-bodies 4a and 4b are respectively provided on opposite ends of the main body 2. The sub-bodies 4a and 4b have a diameter greater than that of the main body 2.

Figure 7B:
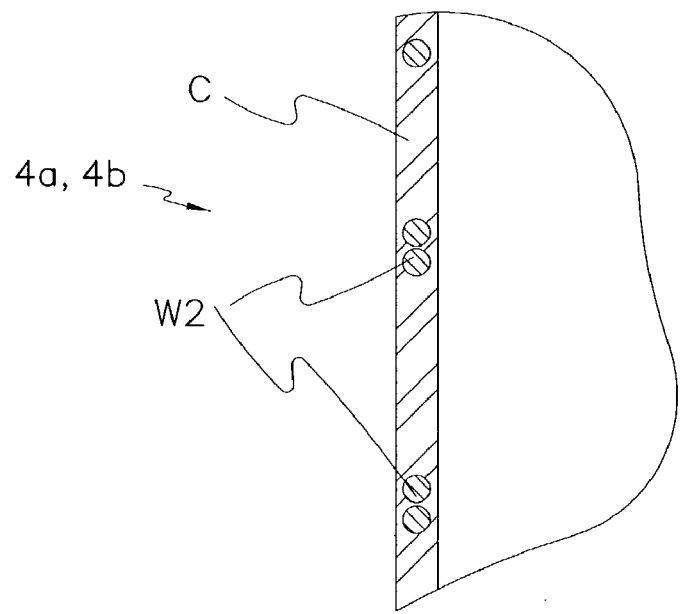
FIG. 7b is an enlarged sectional view of a sub-body of a stent depicted in FIG. 1.

The sub-bodies 4a and 4b have an identical structure to the main body 2. That is, they are formed by sub-wire members W2 and covered with cover member C at their inner and outer circumferences (see FIG. 7b). The sub-bodies 4a and 4b can be integrally formed with the main body 2 by the cover member C formed by the solvent casting.

The size (diameter and length) of the sub-bodies 4a and 4b is designed to be greater than those of passages of body lumen, which are located on the opposite ends of the main body, so as to prevent the main body from displacing from its implanted location of the body lumen. In addition, inverse current preventing means 6 is provided inside the main body 2. The inverse current preventing means 6 functions as a check valve for preventing the food and fluid input from reversely flowing.

Referring to FIGS. 2, 3a, 3b, 4a, and 4b, the inverse current preventing means 6 comprises a fixing layer 6a fixed on the cover member C coated on the inner circumference of the main body 2 and a valve layer extending from the fixing layer 6a. The fixing and vale layer 6a and 6b are also integrally formed with the cover member C by the solvent-casting using solution containing solvent (casting process S1).

As described above, in the casting process S1, the cover member C and the inverse current preventing means 6 are formed.

The fixing layer 6a and the valve layer 6b are formed of an identical material to that of the cover member C. That is, medical polyurethane, silicone-urethane copolymer, silicon, polyamide, polyester or fluoric resin can be used for the fixing and valve layers 6a and 6b. However, other materials that can be easily deformed by outer force and particularly has biocompatibility to minimize the side effect can also be used.

Preferably, a thickness of the fixing and valve layers 6a and 6b is in a range of about 0.01–1.0 mm. When the thickness is less than 0.01 mm, the layers may be easily damaged, and when greater than 1.0 mm, the valve operation cannot be properly realized, resulting in the side effect.

The fixing layer 6a is designed having a length where the fixing layer 6a can be easily bonded on the inner circumference of the main body 2 by the bonding solution B during a bonding process S2. More preferably, the length L1 of the fixing layer 6a is in a range of about 20–50% of the diameter D1 of the main body. When the length L1 is less than the lower limitation of the range, since the bonding area is small, the bonding force is deteriorated, and when greater than the upper limitation of the range, the elastic force of the main body 2 is reduced.

The valve layer 6b are folded toward a central axis of the main body to define three wings 10 that are integrally extended from the fixing layer 6a. That is, the folded wings 10 are connected to each other at their inner ends enclosing the central axis of the stent. The connected inner ends define a passage H that is opened and closed by the operation of the inner ends of the folded wings 10. The folded wings 10 are disposed spacing away from each other by 120° in a circumferential direction.

Preferably, the passage H of the valve layer 6b is designed, when it is closed, to prevent the food and fluid from reversely flowing while allowing gas to pass therethrough. When the passage H is opened, the diameter of the passage H is less than that of the diameter D1 of the main body 2 by the thickness of the valve layer 6b.

Preferably, a length L2 of the valve layers 6b is greater than 150% of the diameter D1 of the main body 2 or greater than 20% of the entire length L3 of the stent. When the length L2 of the valve layer 6b is less or greater than these limitations, the valve operation cannot be smoothly realized, thereby making it difficult to obtain the enough inverse current preventing effect.

Figure 5A:
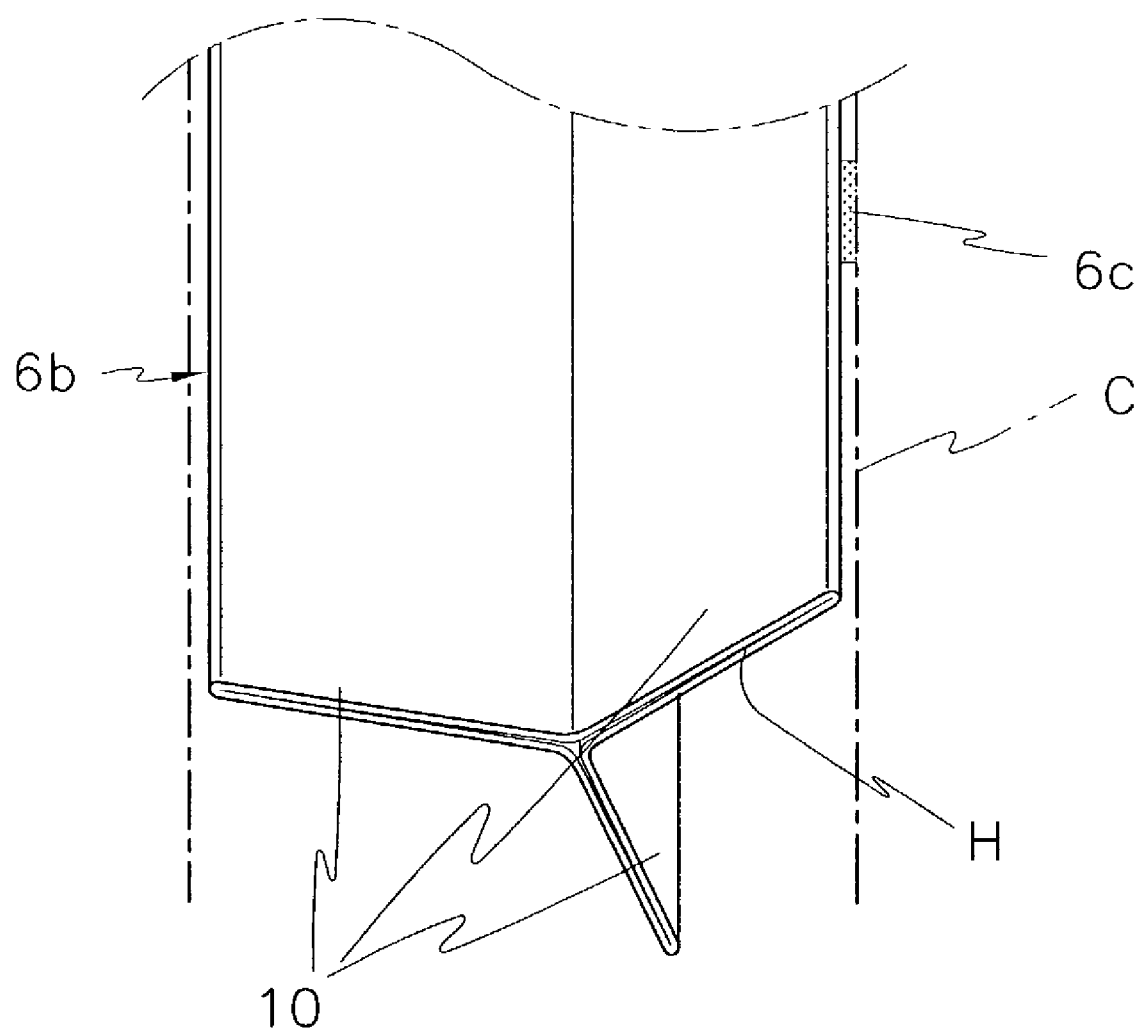
FIG. 5a is a perspective view illustrating a stent having inverse current preventing means according to a preferred embodiment of the present invention, in which the inverse current preventing means is closed.
Figure 5B:
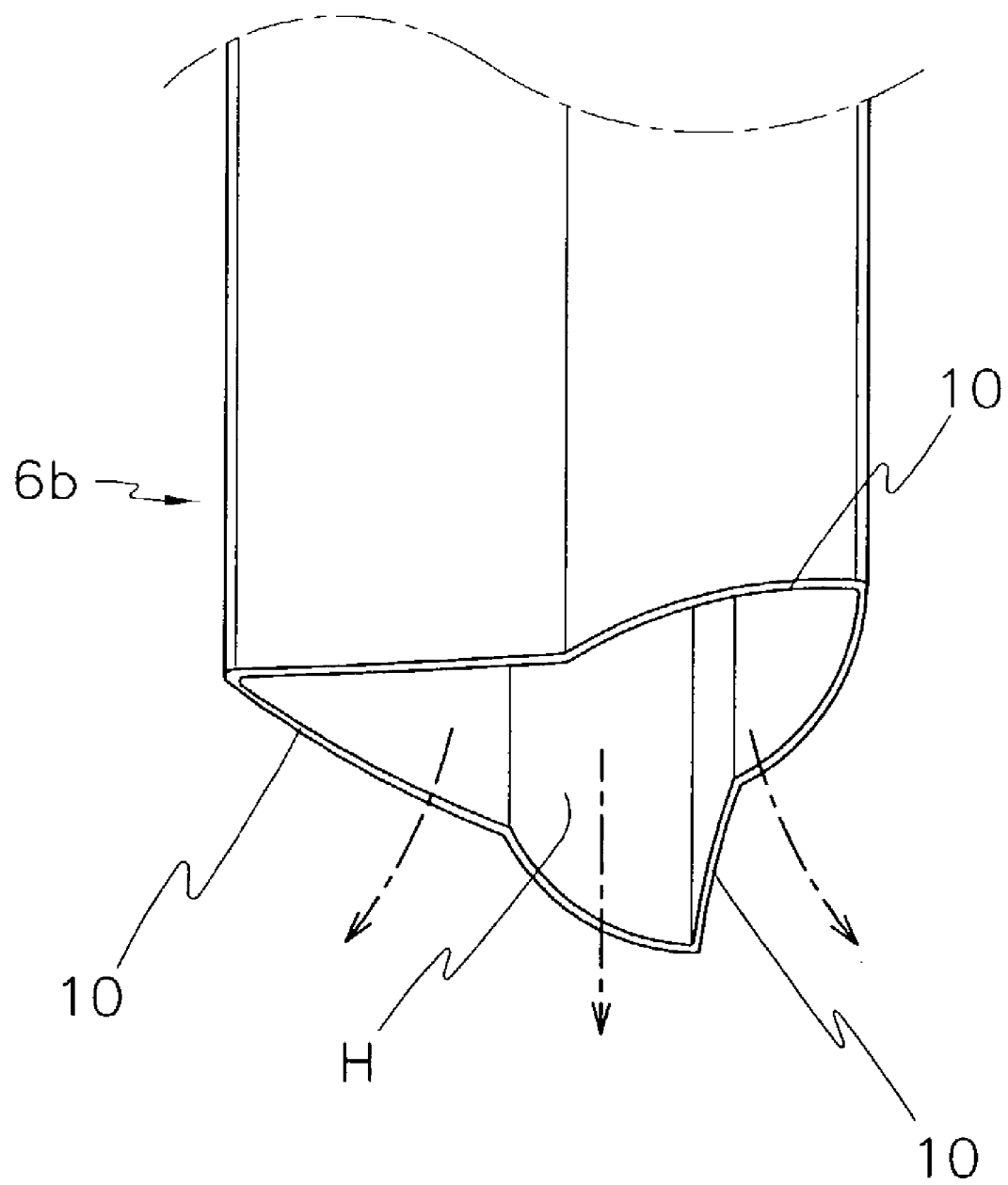
FIG. 5b is a perspective view illustrating the inverse current preventing means that is opened.

As shown in FIGS. 5a and 5b, when the food or fluid is supplied from an upper stream side of the main body, the food or fluid is advanced between the folded wings 10 of the valve layers 6b through the normal open fixing layer 6a, thereby widening the folded wings 10 to open the passage H. After the food and fluid passes through the inverse current preventing means, the folded wings 10 are self-contracted again to close the passage H.

In this embodiment, although the folded wings 10 are disposed spacing away from each other by 120° in the circumferential direction, the present invention is not limited to this. That is, two or more than three wings may be formed.

When more than two folded wings 10 are provided, the valve layer 6b can form the passage H having a diameter almost identical to that D1 of the main body 2.

Figure 6A:
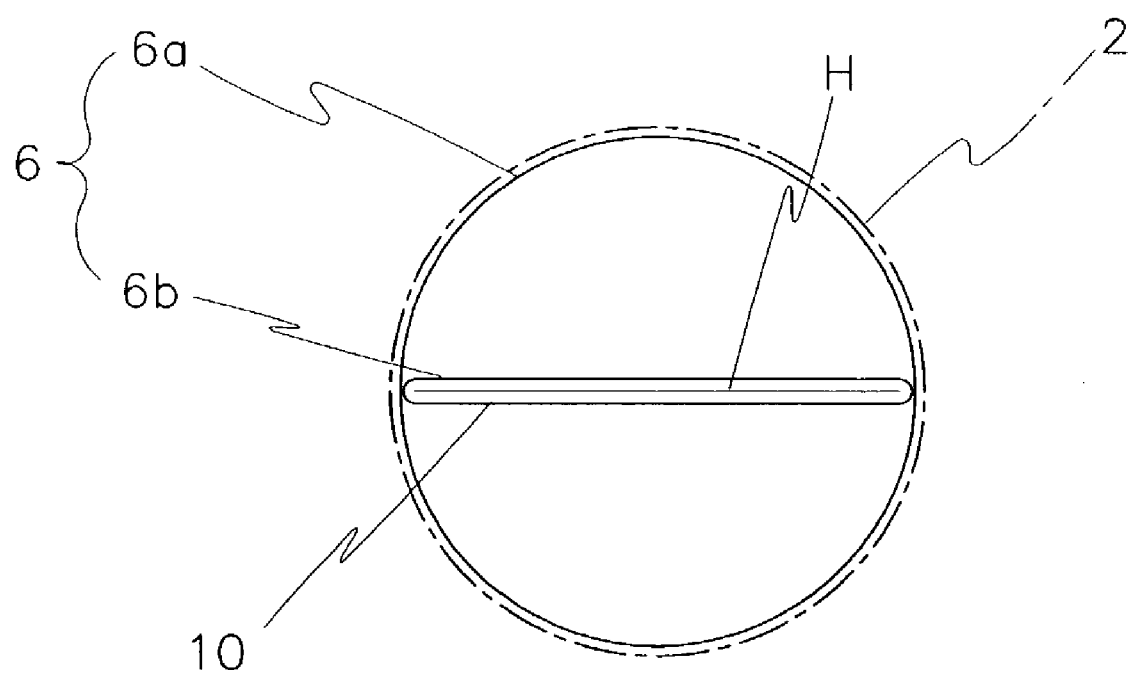
FIG. 6a is a bottom view illustrating an another example of an extended wing of a stent of the present invention.
Figure 6B:
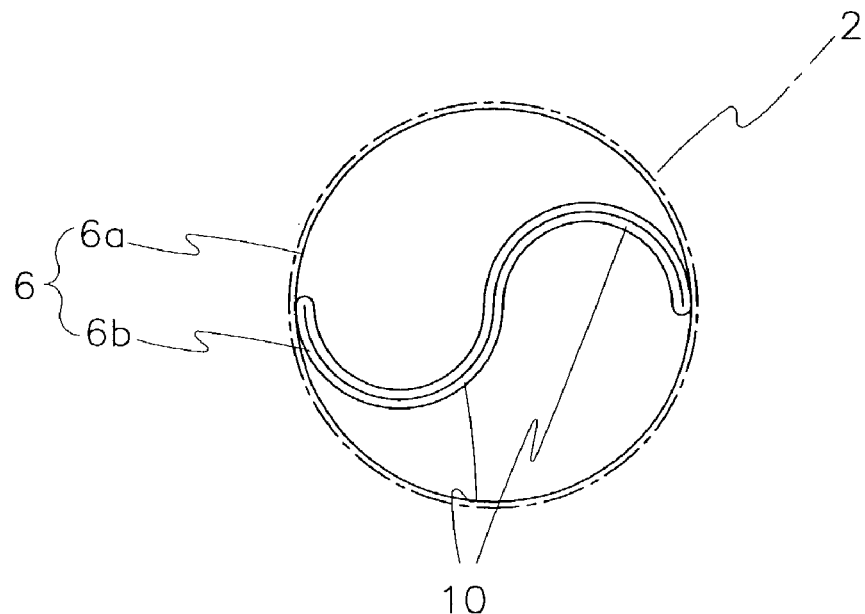
FIG. 6b is a bottom view illustrating an another example of an extend wing of a stent of the present invention.
Figure 6C:
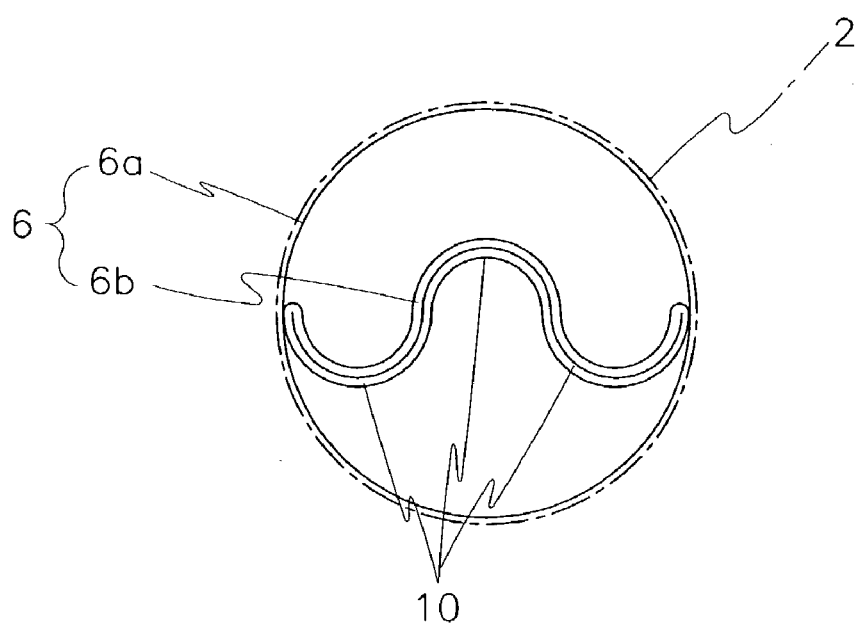
FIG. 6c is a bottom view illustrating an another example of an extended wing of a stent of the present invention.

In the above described embodiment, although the folded wings 10 are formed in a radial direction from the central axis, the present invention is not limited to this. That is, as shown in FIGS. 6a, 6b and 6c, the folded wings can be formed in an inline-shape or a wave-shape.

In addition, although the cover member C and the inverse current preventing means are formed by a solvent-casting, the present invention is not limited to this.

For example, when the cover member C and the inverse current preventing means 6 are formed of fluoric resin based material, it is more preferable that they are be formed by a thermal-bonding process.

After the cover member C is covered on the main body and/or the sub-bodies 4a and 4b and the inverse current preventing means 6 is prepared by the casting process S1, the inverse current preventing means 6 is bonded on the inner circumference of the main body 2 by the bonding process S2. The bonding process S2 is further divided into a setting process S2-1 and a bonding process S2-1.

In the setting process S2-1, the inverse current preventing means 6 is advanced into the main body 2 and set on a bonding position. In FIG. 2, when an upper portion of the main body becomes an upper stream to which the food or fluid is supplied and a lower portion of the main body becomes an lower stream through which the food or fluid is discharged, the inverse stream preventing means 6 is set on a predetermined portion of the inner circumference of the upper stream main body.

When the valve layers 6b are extended over a distal end of the lower sub-body 4b, the extended wings 10 of the valve layers 6b out of the sub-body 4b may stimulate the inner wall of the stomach and disturb the flow of the food from the esophagus to the stomach or the duodenum. Therefore, it is preferable the setting position of the fixing layer 6a is preferably determined within a range where the valve layers 6b are not extended over the distal end of the lower sub-body 4b.

When the bonding position of the inverse current preventing means 6 is set through the setting process S2-1, the inverse current preventing means 6 is fixed on the set position of the main body 2 through the bonding process S2-2.

The bonding process (S2-2) is realized by directly depositing adhesive solution B on a surface of the cover member C contacting the outer circumference of the fixing layer 6a of the inverse current preventing means 6. The deposited adhesive solution B is absorbed in the cover member C by a chemical action and solidified between the fixing layer 6a and the cover member C, thereby fixing the fixing layer 6a on the inner circumference of the main body 2.

The adhesive solution B is formed of a material identical to that for the cover member C and the inverse current preventing means 6. That is, the adhesive solution B is formed of medical Polyurethane, Silicone-Urethane copolymer, Silicone, Polyamide, or Polyester, which contains a solvent in a predetermined ratio, the solvent being selected from the group consisting of DMAC(N,N-DIMETHYLAC-ETAMIDE), DMF(N,N-DIMETHYLFORMAMIDE), DMSO (DIMETHYLSULFOXIDE), THF(TETRAHY-DROFURAN), XYLENE, TOLUENE, CHLOROFORM. An amount of the solvent contained in the adhesive solution B is preferably about 3–70 w %. When the amount is less than the bottom limit of the range, the solution cannot be sufficiently absorbed in the cover member, deteriorating the adhesive force. When the amount is greater than the top limit of the range, the quality of the products may be deteriorated.

Since the adhesive solution B is directly deposited on the surface of the cover member C of the main body 2 to fix the fixing layer 6a of the inverse current preventing member 6, the bonding process S2-2 can be easily performed regardless of the bonding location.

In the above described embodiment, although the fixing layer 6 is bonded on the cover member C formed on the inner circumference of the main body, the present invention is not limited to this.

Figure 8:
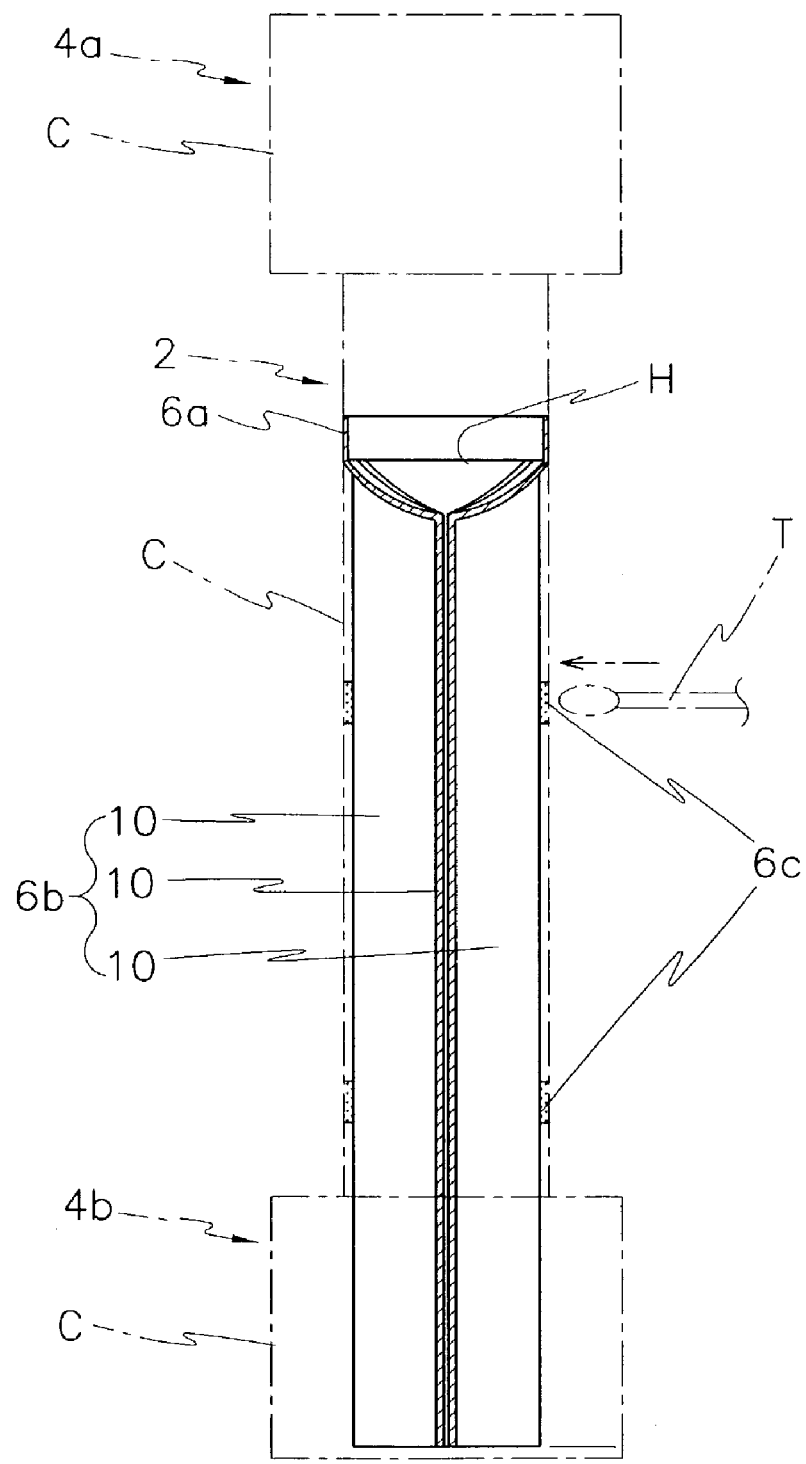
FIG. 8 is a front view illustrating a sub-fixing part of a vale membrane according to a preferred embodiment of the present invention.

Referring to FIGS. 5a and 8, a sub-fixing portion 6c may be formed by depositing the adhesive solution B on at least one point formed on the inner circumference of the cover member 2 in a longitudinal direction so that the valve layer 6b integrally formed with the fixing layer 6a can be fixed on the sub-fixing portion 6c.

The fixing of the valve layer 6b on the cover member C by the sub-fixing portion 6c prevents the valve layer 6b from turning inside out toward the upper stream side during an operation for sucking alien substances from the esophagus-wall of a patient after the stent is implanted within the patient, thereby enhancing the medical reliability.

The above described embodiment does not limit the present invention.

For example, when the cover member C and the inverse current preventing means 6 are made of fluoric resin based material (i.e., PTFE), it is more preferable that they are formed through a thermal bonding process.

Figure 9:
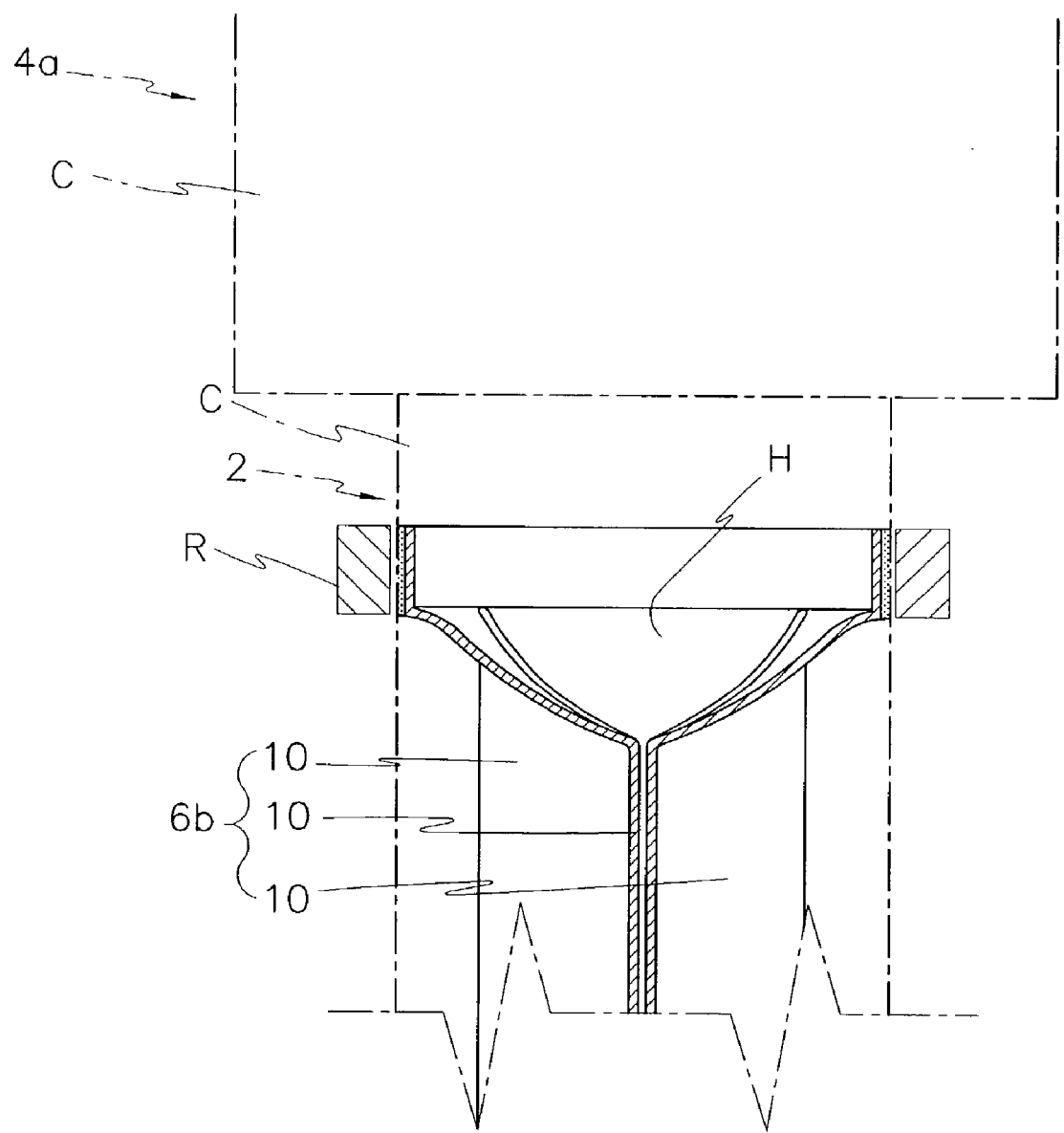
FIG. 9 is a sectional view illustrating a fixing layer of inverse current preventing means according to a preferred embodiment of the present invention.

In the thermal-bonding process, as shown in FIG. 9, after the fixing layer 6a of the inverse current preventing means 6 is first set on the inner circumference of the cover member C of the main body 2 in the setting process (S2-1), the fixing layer 6a and the cover member C are thermally heated by a heater R disposed on a location corresponding to the outer circumference of the main body at a temperature of about 300° C., thereby bonding the fixing layer 6a and the cover member C by the thermal-bonding. During the course of this process, a solution such as PTFE is sprayed to the cover member C to thereby improve the bonding effect.

As described above, since the inverse current preventing means is fixed with a maximum length in the main body, when the stent is implanted in the body lumen, the valve operation can be kept even when the main body or the sub-bodies are deformed or twisted.

In addition, in the manufacturing method, the inverse current preventing means can be easily bonded on the main body regardless of the diameter of the main body and the sub-bodies, thereby improving the productivity and yield.

Furthermore, the valve layer is fixed on at least one fixing point formed on the inner circumference of the cover member of the main body. The fixing of the valve layer on the cover member at more than one fixing point prevents the valve layer 6b from turning inside out toward the upper stream side during an operation for sucking alien substances from the esophagus-wall of a patient after the stent is implanted within the patient, thereby enhancing the medical reliability.

Other embodiments of the invention will be apparent to those skilled in the art from consideration of the specification and practice of the invention disclosed herein. It is intended that the specification and examples be as exemplary only, with a true scope of the invention being indicated by the following claims.

What is claimed is:

1. A stent comprising:
    a cylindrical main body contractible and expandable in a circumferential direction;
    a cover member coated on an inner and/or outer circumference of the main body; and inverse current preventing means for preventing food or fluid from reversely flowing, the inverse current preventing means being disposed in the main body, wherein the inverse current preventing means comprises:
    a generally cylindrical fixing layer having an outer circumferential surface and an inner surface, the inner surface defining a passage having a diameter capable of allowing food and fluid to pass, the fixing layer being fixed in the main body by adhering the outer circumferential surface of the fixing layer to the inner circumference of the main body; and
    a valve layer extending from the fixing layer toward a distal end of the main body, the valve layer comprising an elongate passage formed of a flexible material and extending toward the distal end of the main body, the elongate passage having an opened configuration and a collapsed configuration, the elongate passage comprising:
        at least two creases in the flexible material, the creases extending along the passage generally parallel to the central axis of the main body, wherein the at least two creases are configured to resiliently bias the elongate passage toward the collapsed configuration.

2. A stent of claim 1 wherein a length of the valve layer is about 150% of a diameter of the main body or above 20% of a whole length of the stent.

3. A stent of claim 1 wherein the inverse current preventing means is formed of material selected from the group consisting of medical Polyurethane, Silicone-Urethane copolymer, Silicone, Polyamide, Polyester, and fluoric resin.

4. A stent of claim 1 wherein the cover member is formed of material selected from the group consisting of medical Polyurethane, Silicone-Urethane copolymer, Silicone, Polyamide, Polyester, and fluoric resin.

5. A stent of claim 1 further comprising sub-bodies for preventing the main body from displacing from an implanted position of a body lumen, the sub-bodies being formed on opposite ends of the main body.

6. A stent of claim 1 wherein the valve layer is fixed to at least one point of the inner circumference of the main body at a location other than at the fixing layer.

7. A stent of claim 1 wherein the valve layer is fixed to at least one point of the cover member coated on the inner circumference of the main body, the at least one point at a location other than at the fixing layer.

8. A stent of claim 1 wherein at least one point on at least one of the at least two creases is fixed to the inner circumference of the main body.

* * * * *